United States Patent [19]
Lin

[11] Patent Number: 5,957,883
[45] Date of Patent: Sep. 28, 1999

[54] SYNCHRONOUS VITREOUS LAVAGE DEVICE FOR OPHTHALMOLOGY AND AN OPHTHALMOLOGIC LAVAGING SYSTEM USING THE SAME

[76] Inventor: Po-Kang Lin, 2F, No.283-1, Chang Tsun Road, Taipei, Taiwan

[21] Appl. No.: 08/940,216

[22] Filed: Sep. 30, 1997

[51] Int. Cl.$^6$ ........................................... A61M 1/00
[52] U.S. Cl. ........................ 604/36; 604/38; 604/121; 604/246; 604/181
[58] Field of Search ........................ 604/27, 30, 32, 604/33, 36, 38, 43, 118, 174, 152, 155, 191, 246, 294, 121

[56] References Cited

U.S. PATENT DOCUMENTS

| | | | |
|---|---|---|---|
| 4,650,461 | 3/1987 | Woods | 604/30 |
| 4,909,783 | 3/1990 | Morrison | 604/30 |
| 5,580,347 | 12/1996 | Reimels | 604/27 |

*Primary Examiner*—Wynn Wood Coggins
*Assistant Examiner*—Jennifer R. Sadula

[57] ABSTRACT

A synchronous vitreous lavage device for ophthalmology an includes a platform, a pair of main supporters, an auxiliary supporter, a pair of gears, a pair of movable seats, a pair of screw rods, and a clamp. When the screw rods rotate in different directions, the two movable seats move in opposite direction. Thus, the lavage device simultaneously drains bloody water from the eyeball, and injects lavage water into the eyeball by means of two syringes. The bloody water in the eyeball can be easily removed from the eyeball at a cheap cost. An ophthalmologic lavaging system is formed by connecting two regulating syringes through two three-way valves to the lavage device.

4 Claims, 3 Drawing Sheets

SYNCHRONOUS VITREOUS LAVAGE DEVICE FOR OPHTHALMOLOGY AND AN OPHTHALMOLOGIC LAVAGING SYSTEM USING THE SAME

FIELD OF THE INVENTION

This invention relates to a synchronous vitreous lavage device for ophthalmology, particularly to a lavage device which drains the bloody water out of a patient eyeball and simultaneously injects the lavage water into the eyeball after the patient has been performed an ophthalmological operation. During the lavaging, the pressure in the eyeball is under good control and the lavaging operation is easily done with no bloody water remaining in the eyeball. This invention also relates to an ophthalmologic lavaging system using the above lavage device

BACKGROUND OF THE INVENTION

After a patient has been performed an ophthalmological surgical operation, such as retina surgical operation, some bloody water remains within the patient eyeball and should be removed from the eyeball. Conventional method of removing the bloody water is to perform an additional ophthalmological surgical operation. The conventional method is costly, dangerous and time-consuming.

SUMMARY OF THE INVENTION

It is an object of the Present invention to provide a synchronous vitreous lavage device for ophthalmology. The synchronous vitreous lavage device of this invention comprises a platform, a pair of main supporters, an auxiliary supporter, a pair of gears, a pair of movable seats, a pair of screw rods and a clamp for holding and controlling two lavage syringes. After two syringes are mounted on the lavage device, the finger flanges of the syringes are fixed to the main supporters by means of the engagement of the finger flanges to the main supporters. The thumb rests of the pistons of the syringes are fixed to the movable seats by means of the engagement of the thumb rests to the movable seats. When the handle affixed to the gear is rotated by the turning of the hand, the first screw rod is rotated in one direction and the second screw rod is rotated in the opposite direction. The first movable seat and the second movable seat move in opposite directions. Then, one of the syringes absorbs the bloody water from the eyeball into it, and the other syringe simultaneously injects lavaging water into the eyeball. The absorption and injection of the two syringes are synchronously and isovolemicaly. Thus in the present invention it becomes easy, accurate and convenient to remove the bloody water.

BRIEF DESCRIPTIONS OF THE DRAWINGS

DETAILED DESCRIPTIONS OF THE INVENTION

Figure 1:
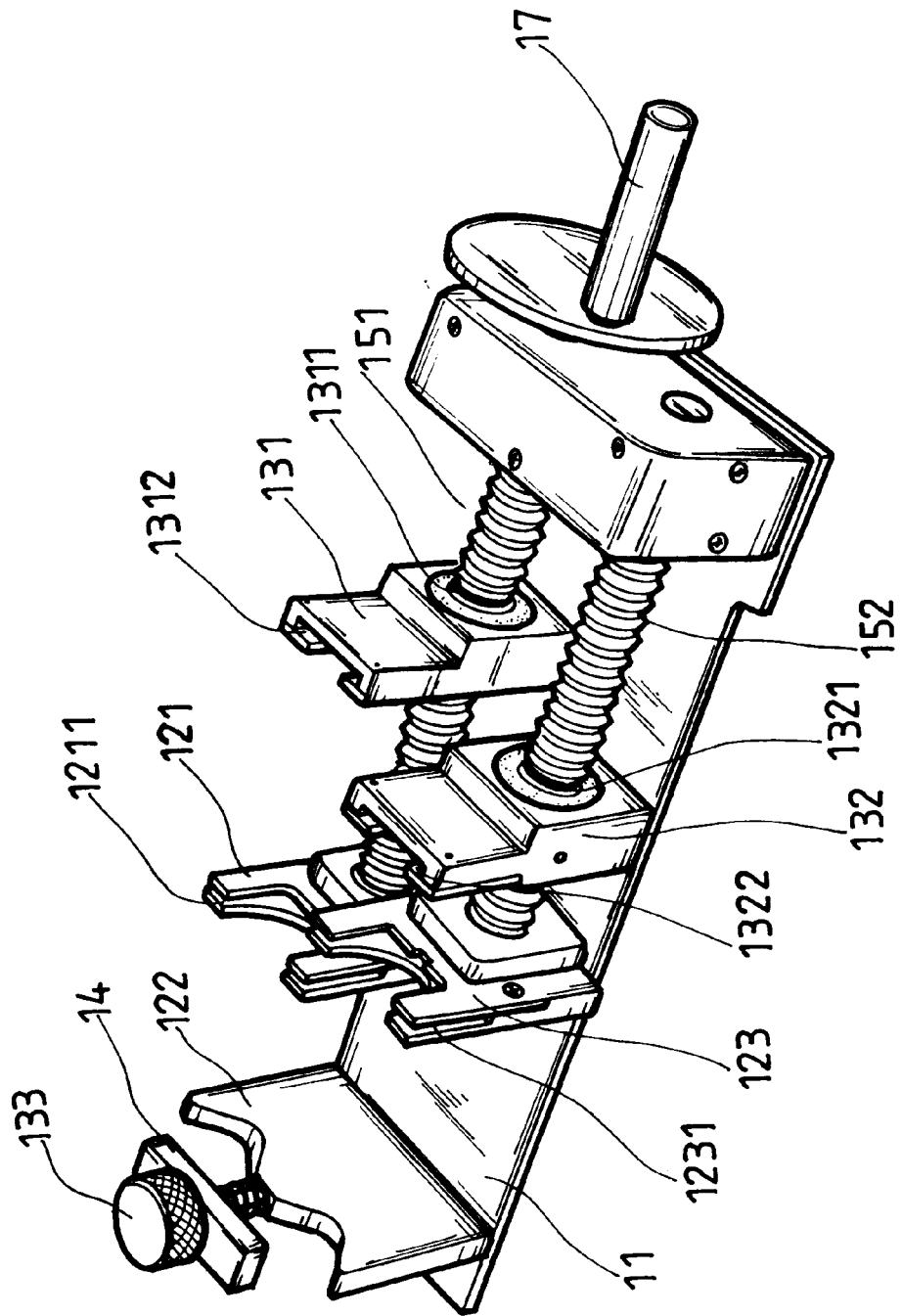
FIG. 1 is an isometric view of the synchronous vitreous lavage device of the present invention.
Figure 2:
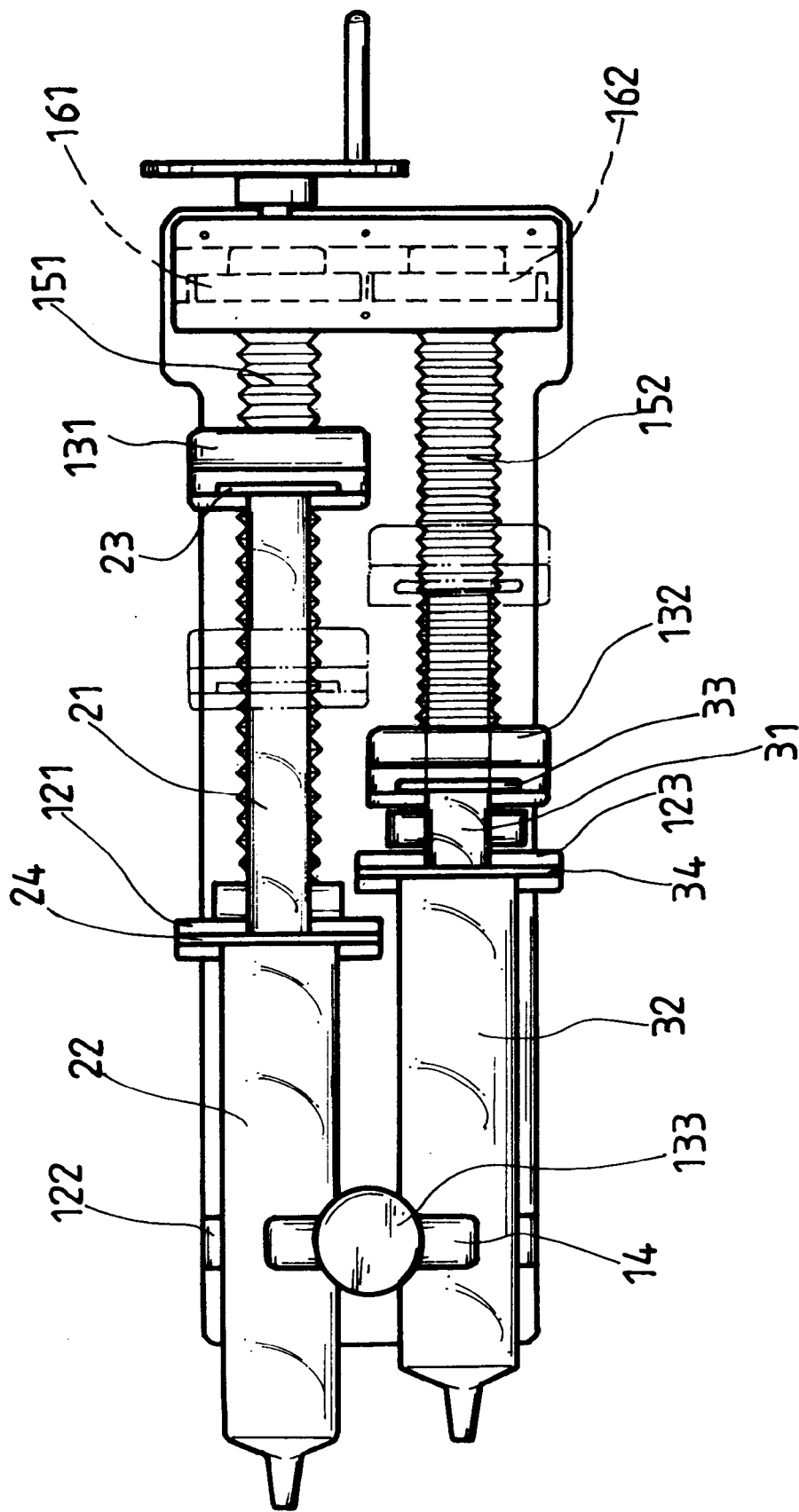
FIG. 2 is a top view of the synchronous vitreous lavage device of the present invention.
Figure 3:
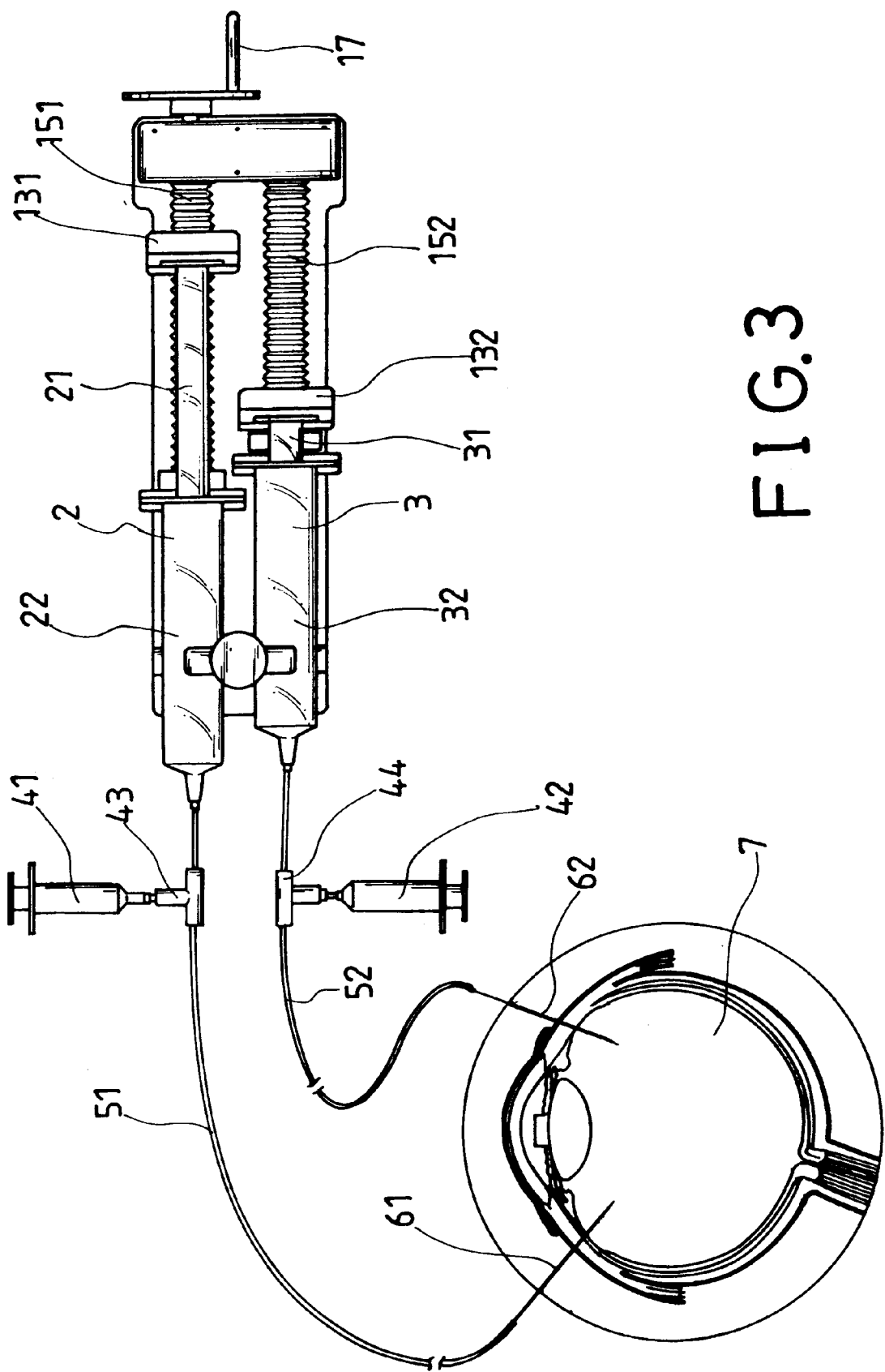
FIG. 3 is a schematic view of the ophthalmologic lavaging system of the present invention.

Please see FIGS. 1–3, a synchronous vitreous lavage device for ophthalmology 1 of the present invention comprises a platform 11, two main supporters 121,123 and an auxiliary supporter 122, two gears 161,162, two movable seats 131,132, two screw rods 151,152, and a clamp 14.

The platform 11 is used to support all other elements of the lavage device 1.

The main and auxiliary supporters 121,122,123 which are fixed on the platform 11, are used to support the syringes 2,3. On each of the main supporter 121,123 there is an engaging slot 1211,1231 onto which each of the finger flanges 24,34 of the syringes 2,3 is inserted for engagement to the supporter 121,123. On the auxiliary supporter 122 the hollow barrels 22,32 of the syringes 2,3 are fixed thereon by means of the clamp 14.

The two gears 161,162 which are mated together on the platform 11 can drive the screw rods 151,152 to rotate in different directions. The gear 161 is driven by a handle 17.

Each of the two movable seats 131,132 has a threaded hole 1311,1321. The two movable seats 131,132 are moved in opposite directions by the rotation of the screw rods 151,152 which pass through the the threaded holes 1311, 1321 of the movable seats.

One ends of the screw rods 151,152 are rotatable about the main supporter 121,123, and the other ends of screw rods 151,152 are connected to the gears 161,162. Each of the screw rods passes through one threaded hole 1312,1322 of the movable seat 131,132. Because the screw rods 151,152 rotate in different directions, the movable seats 131,132 are moved in opposite direction by the driving of the screw rods 151,152. One syringe 2 absorbs bloody water from the eyeball 7, and the other syringe 3 injects lavage water into the eyeball isovolemically simultaneously.

The clamp 14 is used to fix the syringes 2,3 on the auxiliary supporter 122.

Please see FIG. 3 which is a schematic view of the ophthalmologic lavaging system comprising the above synchronous vitreous lavage device, two syringes 2,3, two three-way valves 43,44, two regulating syringes 41,42, two tubes 51,52, and two syringe needles 61,62.

The first ends of the three-way valves 43,44 are connected to the syringes 2,3 respectively, the second ends of the three-way valves 43,44 are connected to the regulating syringe 41,42 respectively, and the third ends of the three-way valves 43,44 are connected to the first ends of the tubes 51,52. The second ends of the tubes 51,52 are connected to the first ends of the two syringe needles 61,62. The other ends of the syringe needles 61,62 are inserted into the eyeball 7 as shown in FIG. 3. We assume that in the hollow barrel 22 is a lavage water to be injected into the eyeball 7 and that in the hollow barrel 32 is the bloody water being absorbed out of the eyeball 7. When the first movable seat 131 moves toward the left side, the piston 21 pushs the lavage water entering the eyeball 7 via the three-way valve 43, the tube 51, and the needle 61. The piston 31 which moves to the right side, absorbs the bloody water in the eyeball 7 via the needle 62, the tube 52, and the three-way valve 44.

The function of the regulating syringes 41,42 is to regulate the amount of the bloody and lavage water in the eyeball, therefore, the pressure in the eyeball 7 is in a normal range, and the shape of the eyeball 7 can be retained. Please see FIG. 3. With the addition of the regulating syringes and the three-way valves, more lavage water can be inserted to the eyeball and additional bloody water can be drained out if necessary.

While the invention has been particularly shown and described with reference to one preferred embodiment, it will be understood by those skilled in the art that various changes in form and details may be made without departing from the spirit and scope of the invention. Although only the preferred embodiment of this invention were shown and described in the above description, it is requested that any modification or combination that comes within the spirit of this invention be protected.

We claim:

1. An ophthalmologic lavaging system comprising:

a platform;

a plurality of main supporters and an auxiliary supporter fixed on said platform;

a plurality of gears mated together and mounted on said platform;

a plurality of movable seats each having a threaded hole;

a plurality of screw rods each having a first end rotatable about a main supporter and a second end connected to said gears, and passing through the threaded hole of a movable seat;

a plurality of main syringes mounted on said main supporters;

a clamp for fixing said main syringes on said auxiliary supporter;

a plurality of regulating syringes;

a plurality of syringe needles; and a plurality of three-way valves each having a first end connected to a main syringe through a tube, a second end connected to a regulating syringe, and a third end connected to a syringe needle through a tube;

wherein one main syringe drains bloody water from an eyeball of a patient and the other main syringe injects lavage water into an eyeball simultaneously through said syringe needles when said screw rods are rotating, and said regulating syringes regulate the amount of said bloody water and said lavage water for maintaining pressure in an eyeball in a normal range.

2. The ophthalmologic lavaging system as claimed in claim 1 further comprising a handle being fixed to one of said gears.

3. The ophthalmologic lavaging system as claimed in claim 1, wherein each of said main supporters has an engaging slot formed thereon and each of said main syringes has a finger flange for being inserted and engaged in said engaging slot.

4. The ophthalmologic lavaging system as claimed in claim 1, wherein each of said movable seats has a movable slot and each of said main syringes has a thumb rest for being inserted and engaged in said movable slot.

* * * * *